United States Patent [19]

Lynch et al.

[11] 4,243,030
[45] Jan. 6, 1981

[54] IMPLANTABLE PROGRAMMED MICROINFUSION APPARATUS

[75] Inventors: Harry J. Lynch, Waltham, Mass.; Robert W. Rivest, Montreal, Canada

[73] Assignee: Massachusetts Institute of Technology, Cambridge, Mass.

[21] Appl. No.: 935,060

[22] Filed: Aug. 18, 1978

[51] Int. Cl.³ .................................................. A61J 7/00
[52] U.S. Cl. ............................ 128/213 R; 128/214 F; 128/260
[58] Field of Search ............... 3/1; 128/261, 260, 213, 128/214 F; 424/19; 417/474–477

[56] References Cited

U.S. PATENT DOCUMENTS

| | | | |
|---|---|---|---|
| 1,874,667 | 8/1932 | Wada | 417/474 |
| 2,447,691 | 8/1948 | Evans | 128/214 |
| 2,896,620 | 7/1959 | Tremblay | 128/214 |
| 3,417,707 | 12/1968 | Zimmer | 417/475 |
| 3,760,806 | 9/1973 | Leeper | 128/260 |
| 3,877,838 | 4/1975 | Choy | 417/474 |
| 3,901,232 | 8/1975 | Michaels et al. | 128/214 F X |
| 4,155,362 | 5/1979 | Jess | 417/477 X |

Primary Examiner—Henry K. Artis
Attorney, Agent, or Firm—Arthur A. Smith, Jr.; Paul J. Cook

[57] ABSTRACT

This disclosure describes an implantable microinfusion apparatus used to deliver an infusate systemically to an animal in accordance with a predetermined temporal program. The apparatus utilizes a pump to provide a hydrostatic force for the discharge of a plastic capillary tubing containing a linearly arrayed program of infusates. The tubing is charged with sequential discrete segments of fluid vehicle containing preselected concentrations of the product or products to be infused. The segments may be delimited by intervals of product-free immiscible fluid or the contents of the program tube may be stabilized by the inclusion of a gel in its fluid composition. The volume of the segments determines the infusion time of the various components of the program; the sequential position of the segments determines the order of their infusion, and the concentration of product in the segments determines the rate of their infusion.

6 Claims, 4 Drawing Figures

IMPLANTABLE PROGRAMMED MICROINFUSION APPARATUS

BACKGROUND OF THE INVENTION

The Government has rights in this invention under Grant No. MH-30870-01, 1R03MSM from the National Institute of Mental Health.

This invention relates to an apparatus for delivering a programmed infusate consisting of quantitatively and/or qualitatively defined products to an animal.

Presently, products such as drugs or hormones are delivered to animals and humans either orally, as bolus injections (intravenous, subcutaneous, etc.), via infusion systems involving external apparatus, tubing connections, or as constant infusions from implanted beeswax pellets, silicone capsules, etc. One such device comprises an osmotic pump marketed by Alza Corporation under the trade name Alzet. The pump consists of a cylinder formed of a collapsible reservoir of flexible, impermeable material surrounded by a layer of an osmotic agent, all of which is surrounded by a rigid semipermeable membrane. When the pump is implanted, it is exposed to an aqueous environment and the osmotic agent imbibes the extracellular fluid at a rate which is controlled by the semi-permeable membrane. The imbibed fluid generates hydrostatic pressure on the flexible, impermeable reservoir, gradually compressing it, producing a constant flow of its content through a delivery portal. Only the product placed into the reservoir leaves the pump since the osmotic agent cannot pass into the reservoir or out of the semi-permeable membrane. The pump rate is therefore fixed and predetermined at manufacture by the selection of the appropriate membrane. Generally, the reservoir is filled with a drug or hormone to be infused at a constant rate in vivo.

A major limitation of this apparatus is that it delivers the product within the reservoir at a constant rate until its content is exhausted. In many instances, constant infusion is undesirable since, for example, many hormones occur rhythmically so that a continuous infusion does not reflect accurately the normal physiological phenomenon. Many hormones, for example, are produced primarily during the night while others are produced primarily during the day.

Accordingly, it would be desirable to provide a means by which the delivery rate and delivery interval of a product from an implantable apparatus could be made variable so that it corresponds more closely to the normal physiological functions of an animal. If this could be done, more meaningful and complete data could be obtained experimentally to provide a more realistic picture of the effects of a product such as a drug or a hormone on an animal. Furthermore, such a means would facilitate the timing of administration of a product or combination of products at various, preselected dose levels, in such a manner as to enhance their therapeutic utility.

SUMMARY OF THE INVENTION

This invention provides a means for delivering an infusate to an animal in accordance with a predetermined program. This mechanism can be made to deliver a product in a manner which corresponds to, or complements, normal physiological rhythms. The device utilized is implantable in the animal and comprises a pump and a tube which contains the product arrayed in a linear program and which is attached to the pump. Sequential segments of the tube contain qualitative and/or quantitative variations in infusate composition. Since the pump operates at a constant rate, timing of product delivery to the animal can be effected by varying the composition and volume of the fluid segments.

DETAILED DESCRIPTION OF SPECIFIC EMBODIMENTS

Figure 1:
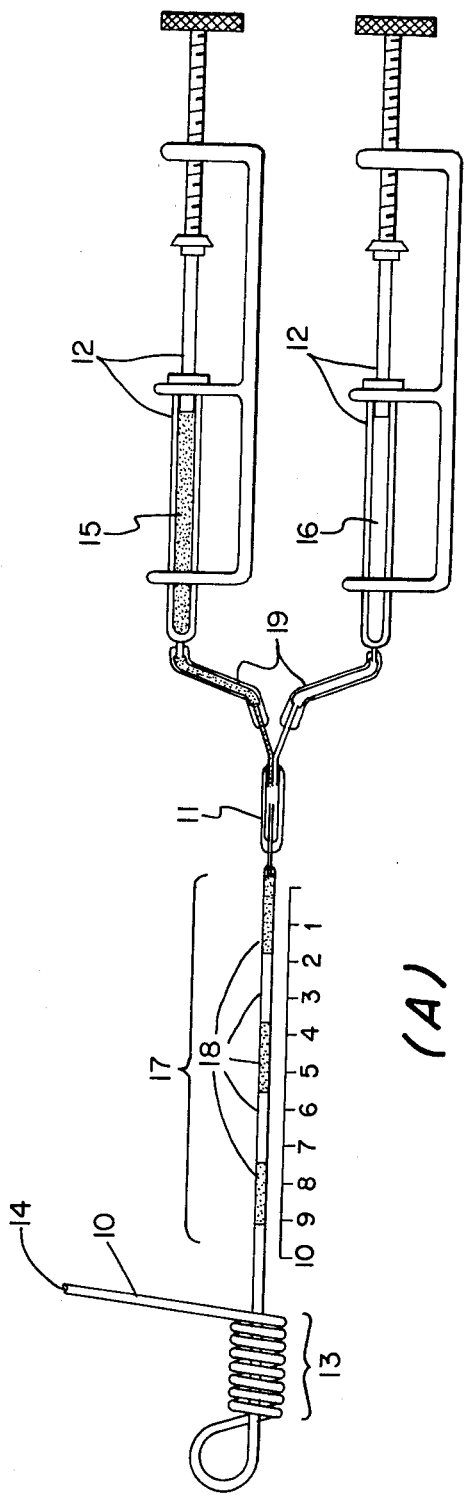
FIG. 1A is a general view of the system used to charge the thermoformed catheter.
FIG. 1B shows the filled tubing with alternating segments ready to be attached to the catheter adaptor of the pump.
FIG. 1C shows the assembled programmed microinfusion apparatus, ready for implantation in an animal; and, FIG. 2 illustrates results of product delivery obtained with the structure of this invention.
Figure 1:
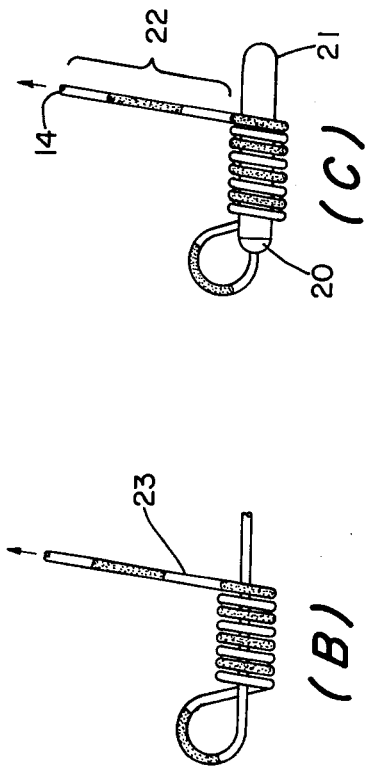

Referring to FIG. 1A, the tubing 10, thermoformed into a spiral coil 13 (to facilitate implantation) is attached to a three- or more-way manifold 11 which, in turn, is attached via capillary tubing 19 to screw driven microsyringes 12, each of which contains one component of the infusate program (15, 16). In a particular instance, the infusate program is composed of two immiscible fluids. Light mineral oil is used as a "spacer" to physically and temporally separate the aqueous components of the program. The latter, for example could consist of melatonin and phenolsulfonphtalein (PSP) in aqueous solution. Additional components can be introduced through the manifold 11 that are either pharmacologically active or serve as spacers. The tubing used is transparent and of uniform bore so the infusate can be readily programmed in the straight, feeder portion 17 of the tube using an external scale (e.g. a conventional metric ruler). 14 refers to the outlet of the catheter.

Referring to FIG. 1B, the linearly arrayed program 18 is forced into the coiled portion 13 with additional physiological saline or other suitable vehicle with a microsyringe 12 through the manifold 11. The feeder portion 17 of the tubing is then cut off.

Referring to FIG. 1C, the coiled tube, charged with program segments 23 (FIG. 1B) is attached via a catheter adaptor 20 to the pump 21 which provides hydrostatic pressure to push the program out of the tubing outlet 14. The programmed microinfusion apparatus is now ready for implantation. The distal, uncoiled portion of the tubing 22 is adjusted to a suitable length to permit discharge of the programmed infusate at a remote site, either subcutaneously, or into the peritoneal cavity, or to serve as a catheter for direct infusion into cerebral ventricles, blood vessels or other organs.

In operation, the water of extracellular fluid enters and activates the pump which exerts pressure on the programmed infusate in tube 10. The linearly arrayed segments of infusate exit sequentially through outlet 14. The time of delivery of a given component of the infusate program is determined by the volume of that component in the tubing and the pressure exerted by the pump. When the pump operates at a constant rate, timing of product delivery is effected by the length of the fluid segments for a given cross-sectional lumen area.

The apparatus of this invention can be used to deliver any product used to treat animals and to test programmed schedules of microinfusion of products on the animal. Thus, for example, the product may be a drug, a hormone, an antigen, a radio-labelled substance or the like.

The constituents of the programmed infusate to be delivered by the apparatus of this invention should be physiologically acceptable and should not degrade the components of the pump or the tube. Suitable agents for use as a relatively immiscible fluid spacer include mineral oil, vegetable oil, gas, e.g. air bubble, etc. The principal of the invention lies in the fact that the segments will remain separated throughout the infusion, thereby permitting a programming of infusate segments. It is to be understood that a relatively inert material need not be used as the spacer but that a plurality of active materials can be delivered in sequence to determine their sequential effect.

The pump needed in this invention to provide pressure to expel the programmed infusate should be implantable in vivo, and be able to generate a constant pressure on the infusate for a number of days. The Alzet osmotic minipump satisfies those requirements: it is implantable in the animal, is activated by the extracellular fluid and a relatively constant pressure is produced for up to a week with the presently available model, regardless of the composition of the programmed infusate.

The following examples illustrate the present invention and are not intended to limit the same.

EXAMPLE I

Figure 2:
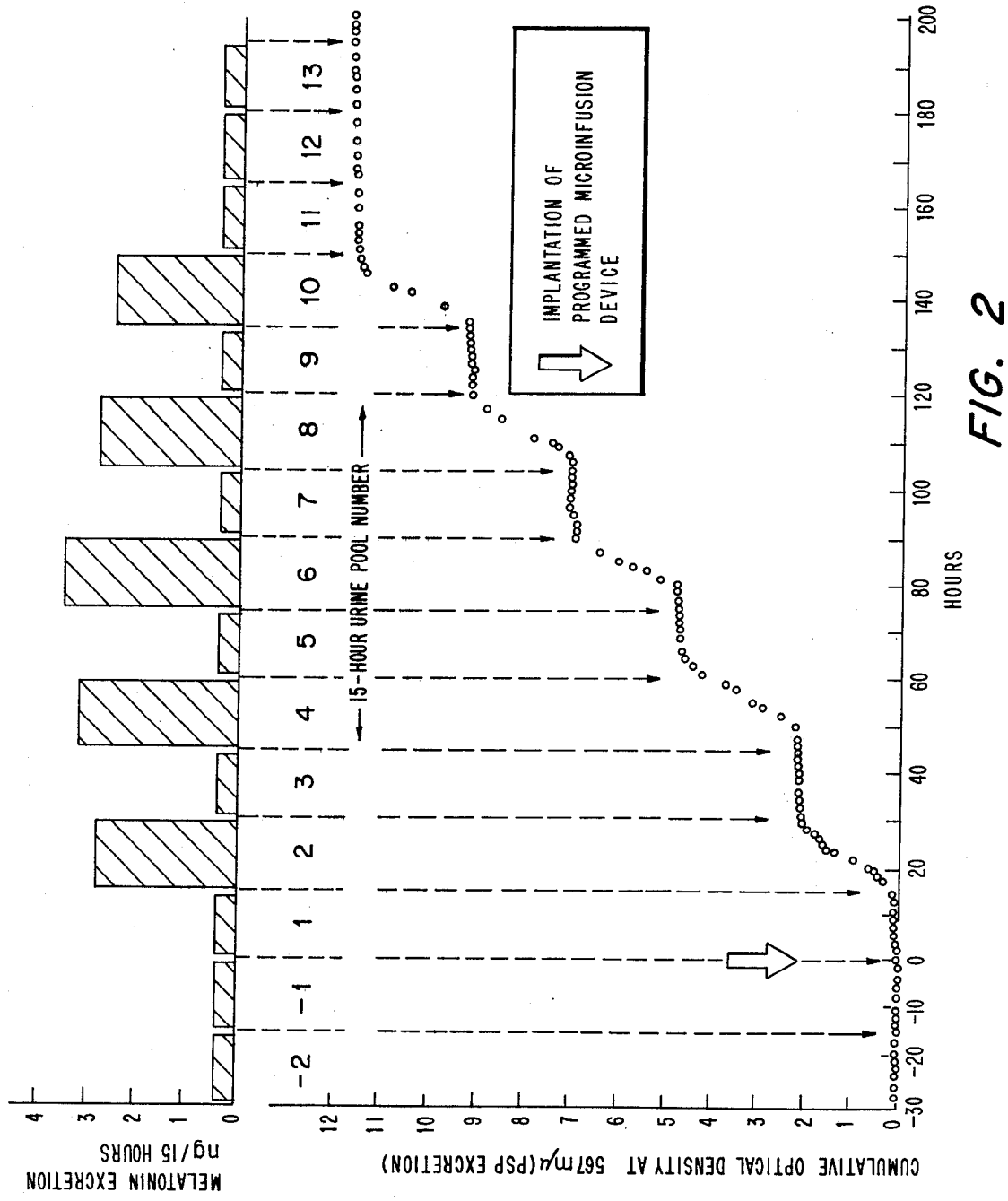

FIG. 2 illustrates how melatonin was recovered in the urine of pinealectomized rats, which have no rhythmic endogenous melatonin synthesis, after implanting subcutaneously a programmed microinfusion apparatus containing alternating segments of melatonin in PSP solution and melatonin-free light mineral oil. The tube containing the programmed infusate has an internal diameter of 0.76 mm and is made of polyethylene.

Urine samples were collected hourly for 200 hours. For 165 hours, urine-colored urine (=normal urine) and PSP-colored (red) urine were excreted cyclically. The optical density of the urine samples was measured at 567 mµ (maximal absorbance of PSP) and plotted cumulatively against time. A stair step curve was produced where the magnitude and slope of the rise reflect quantity and rate respectively of the infusion of the melatonin-in-dye segments of the infusate program, while the length of the tread reflects the duration of infusion of the oil segment. The melatonin content of the various urine fractions, grouped according to the cyclic occurance of PSP in the urine (i.e. 15 hour intervals) is shown by a bar graph in the upper part of FIG. 2: melatonin excretion is rhythmic and concurrent with its rhythmic infusion.

The surgery was performed under ether anesthesia, lasted approximately 5 minutes and required a 2 cm incision on the dorsal midline.

This example shows that the apparatus of this invention can be used to deliver a product to an animal on a rhythmic and regular basis automatically.

EXAMPLE II

Table I illustrates how a programmed infusate composed of segments containing graded concentrations of melatonin alternating with segments of melatonin-free mineral oil results in the appearance of graded quantities of melatonin in the urine of intact rats.

TABLE I

| Concentration of Melatonin | |
|---|---|
| in the segments of the infusate (microgram) | secreted in the urine concurrently with the infusate (nanogram) |
| 0.5 | 1.5 ± 0.2 |
| 1.0 | 2.4 ± 0.7 |
| 2.5 | 3.3 ± 0.1 |
| 5.0 | 4.6 ± 0.5 |

(Mean ± S.E.M.)

A programmed microinfusion apparatus was implanted subcutaneously in each of two rats. The program consisted of segments containing 12 microliters of melatonin in PSP solution alternating with segments containing 5 microliters of melatonin-free mineral oil. The melatonin concentrations used were 0.5, 1.0, 2.5 and 5.0 micrograms of melatonin per 12 microliter segment, and each concentration was replicated in two consecutive aqueous segments. Sequential 20 minute urine samples were collected from each animal and pooled according to the cyclic appearance of PSP in the urine samples (17 hour pools). Melatonin was extracted from each pool and measured. The results shown in Table I demonstrate the correlation between the amount of melatonin infused and the amount of melatonin recovered in the urine.

This example shows that the apparatus of this invention can be used to deliver varying concentrations of a product in a programmed manner automatically.

What we now claim and desire by U.S. Letters Patent is:

1. In an apparatus implantable in an animal which delivers an infusate to the animal, said apparatus including a pump section that exerts a relatively constant pressure on a fluid located within said pump, the improvement which comprises:
   (a) a tube attached to said pump, the interior of said tube being in fluid communication with said fluid located within said pump and
   (b) an infusate located within the interior of said tube, said infusate being divided into segments which are separated by a second fluid located within the interior of said tube comprising a material other than said infusate, said infusate and said second fluid being immiscible thereby to maintain said segments separated within said tube.

2. The apparatus of claim 1 wherein said tube contains at least two different infusates in a segmented array.

3. The apparatus of claim 1 wherein said tube is at least partially spirally wound around said pump.

4. The apparatus of claim 1 wherein said second fluid is a liquid.

5. The apparatus of claim 1 wherein said second fluid is a gas.

6. The apparatus of claim 1 wherein said infusate is in gel form.

* * * * *